(12) United States Patent
Habermann

(10) Patent No.: US 6,531,294 B1
(45) Date of Patent: Mar. 11, 2003

(54) PREPARATION OF PANCREATIC PROCARBOXYPEPTIDASE B, ISOFORMS AND MUTEINS THEREOF AND THEIR USE

(75) Inventor: Paul Habermann, Eppstein (DE)

(73) Assignee: Aventis Pharma Deutschland GmbH (DE)

( * ) Notice: Subject to any disclaimer, the term of this patent is extended or adjusted under 35 U.S.C. 154(b) by 0 days.

(21) Appl. No.: 09/532,730

(22) Filed: Mar. 22, 2000

(30) Foreign Application Priority Data

Apr. 9, 1999 (DE) ......................................... 199 15 938

(51) Int. Cl.[7] .............................................. C12P 21/06
(52) U.S. Cl. .................. 435/68.1; 435/69.1; 435/91.53; 435/220; 435/252.33; 435/320.1; 530/303
(58) Field of Search ............................ 435/68.1, 91.53, 435/219, 220, 252.3, 252.33, 320.1; 530/303

(56) References Cited

U.S. PATENT DOCUMENTS 5,728,543 A * 3/1998 Dorschug et al. .......... 435/68.1

FOREIGN PATENT DOCUMENTS

| EP | 0 347 781 | | 12/1989 |
| EP | 0 448 093 | | 9/1991 |
| EP | 0 504 798 | | 9/1992 |
| WO | 91/03550 | | 3/1991 |
| WO | WO91/06655 | * | 5/1991 |
| WO | WO 95/14096 | | 5/1995 |
| WO | WO 96/0263 | | 2/1996 |
| WO | WO96/23064 | * | 8/1996 |
| WO | WO 96/23064 | | 8/1996 |

OTHER PUBLICATIONS

Hochuli, E. et al., "Genetic approach to facilitate purification of recombinant proteins with a novel metal Chelate adsorbent", Bio/Technology, US, Nature Publishing Co., New York, Nov. 1988, pp. 1321–1325.

Reverter, David et al., "Overexpression of human procarboxypeptidase A2 in Pichia pastoris and detailed Characterization of its activation pathway.", Journal of biological Chemistry, Bd. 273, Nr. 6, Feb. 6, 1988, pp. 3535–3541.

Patrick Aloy et al., "Comparative Analysis of the Sequences and Three–Dimensional Models of Human Procarboxypeptidases A1, A2 and B.", Biological Chemistry, vol. 379, pp. 149–155, 1998.

Jeffrey J. Clare et al., "Production of mouse epidermal growth factor in yeast: high–level secretion using *Pichia pastoris* strains containing multiple gene copies.", Gene, vol. 105, pp. 205–212, 1991.

James M. Cregg et al., "Recent Advances in the Expression of Foreign Genes in *Pichia pastoris*.", Bio/Technology, vol. 11, pp. 905–910, 1993.

J. E. Fox "[32] Carboxypeptidase B (Porcine Pancreas)[1]", Meth. Enzym., vol. 19, pp. 504–508, 1970.

Carol A. Scorer et al., "Rapid Selection Using G418 of High Copy Number Transformants of *Pichia pastoris* for High–level Foreign Gene Expression.", Bio/Technology, vol. 12, pp. 181–182, 1994.

Karen K. Yamamoto et al., "Isolation of a cDNA Encoding a Human Serum Marker for Acute Pancteatitis.", Journal of Biological Chemistry, vol. 267, No. 4, pp. 2575–2581, 1992.

* cited by examiner

*Primary Examiner*—Nashaat T. Nashed
*Assistant Examiner*—Christian L. Fronda
(74) *Attorney, Agent, or Firm*—Heller Ehrman White & McAuliffe, LLP

(57) ABSTRACT

Pancreatic carboxypeptidase B or an isoform or a mutein of carboxypeptidase B may be prepared by (a) expressing a natural or unnatural enzymatically inactive precursor form of carboxypeptidase B in a microorganism by secretion, (b) purifying the precursor form expressed by secretion, and (c) converting the purified precursor form into the active form by an enzymatic treatment. A nucleic acid construct and a host cell containing the construct are useful for preparing pancreatic carboxypeptidase B or an isoform or a mutein thereof by this method.

1 Claim, No Drawings

PREPARATION OF PANCREATIC PROCARBOXYPEPTIDASE B, ISOFORMS AND MUTEINS THEREOF AND THEIR USE

TECHNICAL FIELD

The present invention relates to the preparation of carboxypeptidase B and procarboxypeptidase B and to the use of procarboxypeptidase B for the preparation of carboxypeptidase B which is active in biotechnological processes.

BACKGROUND OF THE INVENTION

Carboxypeptidases are a group of zinc-containing enzymes (proteases) which cleave proteins and peptides, by means of which individual amino acids are hydrolytically removed stepwise from the carboxyl terminus of the proteins or peptides to be degraded. Carboxypeptidases therefore belong to the exopeptidases. Animal carboxypeptidases are formed in the pancreas as precursors (procarboxypeptidases) and are converted in to the active forms by trypsin in the intestine, where they are of great importance for the digestion of peptides, the primary cleavage products of the proteins. According to the substrate specificity, a differentiation is made between various carboxypeptidases.

Carboxypeptidase B releases, for example, exclusively basic amino acids, such as arginine, lysine and ornithine. Carboxypeptidases are useful for determining the sequence of peptides and proteins, because they aid identification of the amino acids on the carboxyl termini of digested polypeptides. Moreover, proteins can be made to measure by use of carboxypeptidase B.

An industrial example of the use of carboxypeptidase B is the preparation of the important pharmaceutical product insulin. The preparation of this peptide hormone is described, inter alia, in European Patent Application EP-A 0 489 780. In this application, carboxypeptidase B is used in an important step in the conversion to insulins of proinsulin structures which have been opened with trypsin.

Carboxypeptidase B, which is used in industrial processes of this type, as a rule originates from carboxypeptidase B preparations, which are commercially obtainable. These are preferably obtained from porcine pancreases (Folk, J. E., *Meth. Enzym.*: 19, 504, 1970).

Enzymes of animal origin, however, have the disadvantage that they can be afflicted by the risk of contamination with animal viruses. The detection of freedom from viruses is complicated and enters as an essential factor into the calculation of the preparation costs. If the enzyme is used in large industrial processes, such as the industrial production of insulin, a further disadvantage lies in high logistics costs of obtaining and storing frozen pancreases.

Biotechnological preparation offers itself as an alternative to the production of carboxypeptidase B by means of the extraction of pancreas tissue. In this process, there are a number of known preparation routes, such as direct intracellular expression or expression via a fusion protein in bacteria, e.g. in the form of a β-galactosidase-carboxypeptidase B fusion protein (*J. Biol. Chem.*, 267:2575–2581, 1992) or corresponding expression in yeast. A further alternative to this is the expression of a carboxypeptidase B precursor, procarboxypeptidase B, which consists of the amino acid sequence of the carboxypeptidase B plus a signal sequence which leads to the secretion of the expression product. Suitable expression systems have been described for *Bacillus subtilis*, Streptomyces, *E. coli* and the yeasts Saccharomyces, Candida, *Hansenula polymorphus* and *Pichia pastoris*. Some of these expression systems are commercially obtainable.

The prerequisite for the use of expression systems for the preparation of carboxypeptidase B is that the growth of the host strain chosen in each case is not inhibited by the presence of active carboxypeptidase B, such that expression is possible in the first place. Host strains which have this property are usually difficult to ferment, such that a relatively poor yield arises over space and time.

One problem with intracellular expression of carboxypeptidase B (direct expression or as a fusion protein) lies in the fact that the protein is initially not present in the correct spatial structure and is thus inactive. It must then be folded in vitro during the purification and processing. In this process, defective folding can occur, which has an adverse effect on the activity and specificity of the enzyme and makes use in the pharmaceutical preparation difficult.

The preparation of carboxypeptidase B by secretion of the mature, active form of the enzyme also shows disadvantages. During the fermentation, carboxypeptidase B is constantly inactivated by the reaction with peptide-like fragments of cellular constituents or constituents of the nutrient medium which are recognized as substrate, such that yield losses occur.

SUMMARY OF THE INVENTION

The invention provides a way out of the aforementioned dilemma, namely the expression and secretion of an inactive carboxypeptidase B form in spatially correct form. By reaction with an enzyme, the active carboxypeptidase B can be prepared from this precursor in vitro. The precursor mentioned can be natural procarboxypeptidase B or a derivative thereof, e.g. an isoform or a mutein or carboxypeptidase B which has been inactivated by addition of a peptide sequence. The nature of the protein sequence added is described in greater detail below.

Accordingly, one subject of the invention is a process for the preparation of pancreatic carboxypeptidase B or of an isoform or a mutein of carboxypeptidase B, where (a) a natural or unnatural precursor form of carboxypeptidase B or an isoform or a mutein of carboxypeptidase B is expressed in a microorganism by secretion, (b) the precursor form expressed by secretion is purified and (c) the purified precursor form is converted into the active carboxypeptidase B or an isoform or a mutein of the carboxypeptidase B by means of an enzymatic treatment;

in particular a process of the type in which the pancreatic carboxypeptidase B or an isoform thereof is human in origin, preferably a process of the type in which the natural precursor form corresponds to procarboxypeptidase B or an isoform thereof.

A particularly preferred process is one of the type in which the unnatural precursor form has the following structure:

$$S—(As)_x—E—CB, \qquad (1)$$

where

S is a signal peptide which brings about the secretion, from the respective microorganism, of the fusion protein formed during expression;

As is any desired genetically encodable amino acid;

E is a peptide linker consisting of an endopeptidase recognition sequence;

CB is the amino acid sequence of carboxypeptidase B or an isoform or a mutein of carboxypeptidase B; and x is an integer from 0–100.

In addition, the invention relates to a process of the type in which a peptide sequence is attached to the natural or unnatural precursor form which makes possible the purification of the precursor form by affinity chromatography, particularly prefer ably a process of the type in which the sequence attached for the purification by affinity chromatography is 1 to 6, preferably 4, histidine residues.

The invention likewise relates to a process of the type where the yeast *Pichia pastoris* is used as a microorganism for expression.

An additional subject of the invention is a process of the type in which the enzymes trypsin, elastase, factor Xa, chymotrypsin or collagenase, preferably trypsin, are used for the enzymatic treatment.

Moreover, the invention relates to a process of the type in which step (c) proceeds under suitable reaction conditions in the presence of an insulin precursor form comprising the B, C and A chains of insulin or of an insulin derivative and in this process mature insulin or a mature insulin derivative is formed, which is isolated from the reaction mixture.

A further subject of the invention is the use of procarboxypeptidase B and carboxypeptidase B in a process of this type.

In addition, the invention relates to a nucleic acid construct for use in a process of this type, comprising a DNA sequence coding for a natural or unnatural precursor form of carboxypeptidase B or an isoform or a mutein of carboxypeptidase B, where the coding sequence mentioned is operatively linked to a promoter which makes possible the expression of the precursor form in a suitable microorganism; preferably the invention relates to a nucleic acid construct in which the DNA sequence codes for a protein of the formula I; in addition, the invention relates to a nucleic acid construct in which a DNA sequence coding for 1 to 6, preferably 4, histidine residues is additionally attached to the DNA sequences coding for a natural or unnatural precursor form of carboxypeptidase B or an isoform or a mutein of carboxypeptidase B.

The invention like wise relates to a process for the preparation of a nucleic acid construct of this type, where (a) the DNA sequences mentioned are isolated or prepared, and (b) are inserted into a vector in a suitable manner.

Moreover, the invention relates to the use of a nucleic acid construct of this type in an abovementioned process for the preparation of pancreatic carboxypeptidase B.

The invention also relates to a host cell, comprising an abovementioned nucleic acid construct and a process for the preparation of a host cell of this type, in which an abovementioned nucleic acid construct is included in a suitable microorganism.

The invention also relates to the use of a host cell of this type in an abovementioned process for the preparation of pancreatic carboxypeptidase B.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

The invention provides expression and secretion, in spatially correct form, of an enzymatically inactive natural or unnatural precursor form of carboxypeptidase B in a microorganism by secretion. The active carboxypeptidase B can be converting from this precursor in vitro by reaction with an enzyme.

"Active carboxypeptidase B" means a carboxypeptidase B which is found in nature, e.g. carboxypeptidase B of man or naturally occurring isoforms thereof. "Active carboxypeptidase B" can also mean a mutein of the naturally occurring carboxypeptidase B, in which deletions, additions or substitutions of the amino acid sequence occur, but the enzymatic activity of the mutein corresponds qualitatively to the enzymatic activity of naturally occurring carboxypeptidase B. Procarboxypeptidase B or a derivative thereof is preferred, because the active carboxypeptidase B can be prepared from this protein in a surprisingly readily controllable manner. Moreover, procarboxypeptidase B and the derivatives thereof mentioned can be stored over relatively long periods of time, whereas a loss of activity is observed on the storage of carboxypeptidase B.

The derivatives of procarboxypeptidase B mentioned contain the amino acid sequence of carboxypeptidase B plus an N-terminally attached peptide having the amino acid sequence of a signal peptide for the exclusion of the derivative from the host organism used for expression, optionally any desired amino acid sequence up to 100 amino acids long and an endopeptidase recognition sequence which makes possible the enzymatic removal of the additionally N-terminally attached peptide from the carboxypeptidase B portion of the derivative. Examples of endopeptidase recognition sequences of this type are the corresponding known recognition sequences of trypsin, factor Xa, elastase, chymotrypsin and collagenase.

Surprisingly, it has moreover been found that procarboxypeptidase B can react with proinsulin and trypsin in one reaction vessel, such that the freshly formed active carboxypeptidase B immediately recognizes and hydrolyses the resulting carboxy-terminal arginines of the insulin B chain. The carboxypeptidase B resulting during the process is more active than that carboxypeptidase B which was previously stored and then added to the reaction with proinsulin. The trypsin present in the reaction mixture serves not only for the activation of procarboxypeptidase B, but also cleaves proinsulin specifically and thus contributes to the release of mature insulin.

The kinetics of activation by trypsin are surprisingly not adversely affected by the addition of a tetra-His sequence at the N terminus of the procarboxypeptidase B or the derivatives mentioned. The advantage of such an addition lies in the fact that the protein thus can be purified readily by affinity chromatography by means of nickel chelate complexation. The use of such modified procarboxypeptidase B is likewise a subject of the invention.

By way of example, the cDNA sequence of human pancreatic procarboxypeptidase B is expressed. However, the DNA sequence of other species could be used instead of the human DNA sequence, because of the substantial identity among the human gene and the corresponding genes from cattle, rats, pigs or other species. The sequence similarity among these genes is reflected in substantial identity among the encoded proteins. The corresponding DNA coding for muteins of carboxypeptidase B can also be used. Likewise, DNA sequences which code for natural or artificially produced isoforms of carboxypeptidase B or of procarboxypeptidase B can be used. Moreover, of course, all those DNA sequences which do not occur naturally can be used which, on account of the degeneracy of the genetic code, can replace the aforementioned DNA sequences that codes for a carboxypeptidase B or procarboxypeptidase B or in each case a mutein thereof.

The *Pichia pastoris* expression system obtainable commercially through Invitrogen is likewise used by way of example for the secretion of heterologous proteins for the production of human procarboxypeptidase B. It is clear to the person skilled in the art that bacterial systems, e.g. *E. coli* secretor mutants, such as have been described in European Patent Application EP-A-0 448 093, can also be used if the hirudin sequence described there is replaced by the sequence of the procarboxypeptidase. A further alternative would be the expression of the human procarboxypeptidase B in Streptomycetes, such as, for example, described in European Patent Application EP-A 0 504 798 in the case of the expression of glutarylamidase.

It is likewise clear that in the large industrial use of the process for the isolation of relatively large amounts of enzyme other protein purification steps than described in the examples, such as are prior art, can be used.

In the case of reference to the described process, as a rule the expression "a process of this type" is used if reference is not expressly made to another process. "Natural" and "unnatural" precursor forms of carboxypeptidase B are molecules of the type which occur in nature ("natural precursor forms") or which have arisen from natural precursor forms of this type by substitution, addition or deletion of amino acids ("unnatural precursor forms"), where the unnatural precursor forms can be converted into active pancreatic carboxypeptidase B or isoforms or muteins thereof by an enzymatic treatment.

In the case of reference to the described nucleic acid construct, as a rule the expression "a nucleic acid construct of this type" is used if reference is not expressly made to another nucleic acid construct.

The present examples are intended to illustrate how procarboxypeptidase B and (His)4-procarboxypeptidase B could be expressed and purified. Moreover, it is explained how procarboxypeptidase B could be activated with trypsin, namely both in isolated form and on the combined use of trypsin and procarboxypeptidase B for the preparation of insulin.

EXAMPLES

The following examples are intended to illustrate, but not limit, the scope of the invention.

Example 1

The example describes the preparation of a recombinant *P. pastoris* strain for the secretion of human procarboxypeptidase B. The starting material used is a cDNA preparation such as is prepared according to known methods from RNA which was isolated from human pancreatic tissue. cDNA preparations of this type are commercially obtainable, for example from Clontech (catalog No. 7410-1). For the amplification of the desired cDNA target sequence, two primers are synthesized. The sequences for this are taken from the gene bank database. The cDNA sequence for human pancreatic carboxypeptidase B is found under the accession number M81057. The forward primer sequence P-CPBf22 corresponds to the region 22bp–32bp and the backward primer sequence P-CPBrev1271 corresponds to the region 1271bp–1250bp. For amplification, a standard polymerase chain reaction (PCR) is carried out. The reaction products of the PCR are separated by gel electrophoresis and the resulting DNA band of the expected length of about 1250bp is eluted and reacted in a ligation reaction with the pCR® vector of the Original TA Cloning® kit from Invitrogen. Competent cells of the strain *E. coli* INVα F', additionally supplied as a constituent of the kit, are transformed with the ligation mixture and plated out and incubated at 37° C. on NA plates that contain 25 mg/liter of ampicillin. Cells taken from the grown colonies are resuspended the next morning in 20 μl of sterile water and incubated at 94° C. for 10 minutes. PCR reaction buffer, which in each case contains 0.2 μg of the two primers P-CPBf22 and P-CPBrev1271, is then added to the suspension such that a standard PCR can be carried out in a reaction volume of 100 μl. The reaction products are then analyzed by gel electrophoresis. Desired transformants contain DNA that can be amplified to give an approximately 1250 bp fragment. Plasmid DNA is isolated from one of the clones defined in this way and the inserted cDNA sequence is completely characterized by means of sequence analysis. The determined sequence is completely identical to the sequence published by Aloy et al. (Biol. Chem., 379:149–155, 1998 ). According to the publication, the codons which encode the amino acids −95 to 307 of the procarboxypeptidase are used for expression. The expression vector used is the plasmid pPIC9, which was described by Cregg, J. M. et al. (Bio/Technologie, 11:905–910, 1993) and Scorer, C. A. et al. (Bio/Technologie, 12:181–184, 1994). For this, the plasmid pPIC9 is opened using the restriction enzymes XhoI and EcoRI. For insertion of the cDNA sequence into the vector, two primers are synthesized. The forward primer PPICCPBf has the sequence

```
                                        (SEQ ID NO.: 1)
         XhoI         Procarboxypeptidase →
5' TTTTTTCTCGAGAAAAGACATCATGGTGGTGAGCAC 3'
``` and the backward primer PPICCPBrev has the sequence

```
                                        (SEQ ID NO.: 2)
         EcoRI              Procarboxypeptidase
5' TTTTTTGAATTCCTTACTACTAGTACAGGTGTTCCAGGAC 3'
```

In a standard PCR reaction, the cDNA is amplified using the two primers and the resulting fragment is digested with the enzymes XhoI and EcoRI after purification. This made-to-measure fragment is precipitated from the reaction mixture, taken up in water and reacted with the opened vector fragment in a ligase reaction. Competent INVαF' cells are transformed using the ligation mixture and plated out on selection plates. Colonies which contain the desired expression plasmid are identified by means of PCR technology as described. Plasmid DNA is obtained from a clone recognized as correct. This DNA is introduced as described by Cregg J. M. et al. into the *P. pastoris* strain GS115, which is auxotrophic for histidine (Scorer C. A. et al. Biotechnology, 12:181–184, 1994). Colonies that, after transformation, have become prototrophic for histidine are investigated for expression of the procarboxypeptidase protein. For this, 50 clones are expressed, such as described by Clare, J. J. et al. (Gene, 105:205–212, 1991). At the end of the expression, 1 ml of culture medium is removed, the cells are removed by centrifugation and the clear supernatant is freeze-dried. Aliquots of the supernatant are analyzed by means of SDS polyacrylamide gel electrophoresis. After Coomassie Blue staining, a clear band is visible in samples of some of the supernatants in the range of 45,000 Da molecular weight, which is not observed in samples of supernatants of noninduced cultures. This band is clearly recognized in the Western Blot analysis of the anti-porcine carboxypeptidase B antibody from Chemicon (order No.

AB1801). A 100 ml culture, which expresses procarboxypeptidase B and is isolated according to Example 2, of the clone which produces the best yield in this experiment is cultured in a 2 l cross-baffle shaker flask.

Example 2

The example describes the purification of human procarboxypeptidase B from supernatants of culture broths according to Example 1. First, the cells are removed by centrifugation. The clear supernatant is then treated with ammonium sulfate until an approximately 55% saturation is achieved. The precipitated protein is removed by centrifugation and the pellet is dissolved in 5 ml of a 50 mM Tris HCl (pH 7.5) solution comprising 1 mM EDTA. The protein suspension is then separated by means of DEAE cellulose chromatography. The elution chromatogram is plotted over a 0 to 0.5 M NaCl gradient. The fractions which contain the desired protein are identified by means of Western Blot analysis. The fractions are combined and concentrated by means of ultrafiltration. The concentration of protein in the retentate is determined by means of the protein determination according to Bradford. The procarboxypeptidase enriched in this way is then freeze-dried for storage or activated directly according to Example 4 by means of trypsin treatment. The Coomassie Blue staining of the material separated by gel electrophoresis shows that approximately 60% of the material is found in a protein band of about 45,000 Da molecular weight. The band corresponds to the region identified in the Western Blot.

Example 3

The example describes the preparation of the expression vector for the synthesis of $(His)_4$-procarboxypeptidase B. The construction is carried out according to the route described in Example 1. The primer PPICCPBrev is used (see Example 1). The forward primer is modified such that it contains four additional codons for histidine. The sequence of the primer PCPBHisf accordingly reads:

```
                                              (SEQ ID NO.: 3)
         XhoI                       Procarboxypeptidase →
5' TTTTTTCTCGAGAAAAGACACCATCACCACCATCATGGTGGTGAGCAC 3'
                      (His)4
```

The *P. pastoris* strain constructed in this way is used for expression and the HIS-procarboxypeptidase B protein is directly purified by means of a nickel affinity chromatography step after precipitation with ammonium sulfate in solution. The chromatographic support material used is "ProBond™ NICKEL Chelating Resin" (Invitrogen catalog No. R801-01) corresponding to the details of the manufacturer. After Coomassie Blue staining, analysis by gel electrophoresis shows virtually only one visible band, which has a molecular weight of about 45,000 Da. This band is recognized by the antibody employed in the Western Blot experiment. The material purified in this way is ultrafiltered and, after protein determination according to the method of Bradford, either freeze-dried for storage or directly activated according to Example 4.

Example 4

The example describes the activation of procarboxypeptidase B by reaction with trypsin. For this, 22 mg of freeze-dried material from Example 2 are dissolved in 14 ml of a 0.1 molar tris HCl solution (pH 7.8), heated to 26° C. and mixed with 15 μl of a trypsin solution (0.1 U/ml) and incubated with stirring for 3 hours. The solution is then mixed with a soybean trypsin inhibitor and the trypsin, the inhibitor, the propeptide fragments removed from the carboxypeptidase B and other constituents are separated off from the carboxypeptidase B by microfiltration by means of a Centriprep filter unit (Amicon) having a molecular weight exclusion limit of 30,000 Da. The active carboxypeptidase B is stored frozen in a 5 mM tris buffer (pH 7.5). The specific activity is determined after determination of the protein concentration according to the procedure of Folk, J. E. (Meth. Enzym., 19:504–508, 1970). If the starting material has been prepared according to Example 3, only 15 mg of the starting material are used for activation.

Example 5

The example describes the combined use of trypsin and procarboxypeptidase B for the preparation of insulin from mono-Arg insulin. Example 6 of European Patent Application EP-A 0 347 781 describes the reaction of mono-Arg insulin with trypsin and carboxypeptidase B in one reaction vessel. In the present example, the carboxypeptidase B in Example 6 of European Patent Application EP-A 0 347 781 is now replaced by 15 μg of procarboxypeptidase B from Example 2 of this application or by 10 μg of procarboxypeptidase B from Example 3 of this application. In both reactions, the trypsin concentration is increased by employment of 3 μl of trypsin instead of 2.5 μl of the stock solution (according to Example 6 of European Patent Application EP-A 0 347 781).

This invention is disclosed in German Patent Application No. 19915938.6–41, filed Apr. 9, 1999, which is herein incorporated by reference in its entirety.

What is claimed is:

1. A method of producing mature insulin or a mature insulin derivative comprising:
  (a) expressing a precursor form of carboxypeptidase B in a host cell, wherein said host cell comprises a nucleic acid construct comprising
    (i) a sequence that codes for a natural precursor form of carboxypeptidase B, wherein the precursor form comprises a secretion signal sequence, is enzymatically inactive, and is capable of being converted to an enzymatically active form by enzymatic treatment, and
    (ii) a promoter that is operatively linked to the coding sequence, where the promoter is capable of expression in a microorganism
  (b) purifying the precursor form of carboxypeptidase B,
  (c) adding together in one reaction mixture, said purified precursor form of carboxypeptidase B, trypsin and an insulin precursor comprising the B, C and A chains of insulin or an insulin derivative, thereby converting the purified precursor form into the active carboxypeptidase B and producing mature insulin or a mature insulin derivative and
  (d) isolating the mature insulin or a mature insulin derivative from the reaction mixture.

* * * * *